United States Patent [19]

Zito

[11] Patent Number: 5,405,584
[45] Date of Patent: Apr. 11, 1995

[54] DEVICE FOR DETECTING ADSORBED MOLECULES

[76] Inventor: Richard R. Zito, 330 N. Mathilda Ave. (#606), Sunnyvale, Calif. 94086

[21] Appl. No.: 863,422

[22] Filed: Apr. 3, 1992

[51] Int. Cl.[6] ............................................. G01N 27/60
[52] U.S. Cl. .................................... 422/90; 250/253; 250/255; 250/472.1; 422/88; 422/91
[58] Field of Search .................... 422/90, 88, 91; 250/255, 253, 472.1; 324/72, 60

[56] References Cited

U.S. PATENT DOCUMENTS

| | | | |
|---|---|---|---|
| 3,525,936 | 8/1970 | Vosteen | 324/72 |
| 3,652,932 | 3/1972 | Sessler et al. | 324/72 |
| 3,778,229 | 12/1973 | Webster et al. | 422/90 |
| 3,852,669 | 12/1974 | Bowman et al. | 325/151 |
| 3,887,877 | 6/1975 | Vosteen | 324/72 |
| 4,147,981 | 4/1979 | Williams | 324/32 |
| 4,197,493 | 8/1980 | Juve et al. | 324/72 |
| 4,243,631 | 1/1981 | Ryerson | 422/90 |
| 4,339,721 | 7/1982 | Nihira et al. | 324/457 |
| 4,744,954 | 5/1988 | Campbell et al. | 422/90 |
| 4,763,078 | 8/1988 | Williams | 324/458 |
| 4,835,461 | 5/1989 | Snelling | 324/109 |
| 4,853,536 | 8/1989 | Dempsey et al. | 250/253 |
| 4,938,928 | 7/1990 | Koda et al. | 422/90 |
| 5,055,674 | 10/1991 | Kotrappa | 250/255 |
| 5,065,030 | 11/1991 | Perlman | 50/472.1 |
| 5,068,538 | 11/1991 | Harley | 250/472.1 |

FOREIGN PATENT DOCUMENTS 1-284052  4/1989  Japan .
3-235048  10/1991  Japan .

OTHER PUBLICATIONS

Zita, R. R., "Removal of Adsorbed Gases with $CO_2$ Snow," in SPIE (Society of Photo–Optical Instrumentation Engineers) vol. 1494, pp. 427–433, Apr. 4, 1991.

Primary Examiner—Timothy M. McMahon

[57] ABSTRACT

A elecret substrate (10), which is exposed to the environment so as to collect molecular contamination, lies at the bottom of a holder (20). Above the substrate a sensor head (100) is supported. Signals from the sensor head are relayed to an electrostatic voltmeter (130). The voltage reading at electrostatic voltmeter (130) is a function of the amount of polar molecule contamination on substrate (10).

1 Claim, 2 Drawing Sheets

DEVICE FOR DETECTING ADSORBED MOLECULES

BACKGROUND—FIELD OF INVENTION

This invention describes a device for detecting polar molecular contamination on surfaces and for measuring dipole moments of polar molecules.

BACKGROUND—DESCRIPTION OF PRIOR ART

It is a well known fact that gaseous polar molecules will "wet" a surface which is also composed of polar molecules. The phenomenon accounts for, among other things, the growth of rain drops around seeding nuclei (B. J. Mason, *The Physics of Clouds*, 2nd ed., Clarendon Press, Oxford, 1971 p. 226). If a seeding nucleus molecule has, say, its electropositive end residing on the surface of the nucleus, then the electronegative end of gaseous molecules will be attracted to it, and cover it, resulting in the growth of a drop. This simple piece of physics can be used for detection of adsorbed polar molecules. It turns out that molecules of Teflon-brand PTFE (Teflon is a trademark of E. I. duPont de Nemours & Co., Wilmington, Del.) are also polar, and if a piece of Teflon is heated in the presence of a strong eternally applied electric field, molecules of Teflon will align themselves with the field. If the heat source is then removed, the Teflon will be left with a permanent polarization. One side of the Teflon will have a permanent positive charge, and the other side a permanent negative charge. Such a material is called an electret (P. Lorrain, D. Corson, *Electromagnetic Fields and Waves*, 2nd Ed., W. H. Freeman, San Francisco 1962, p. 113). An electrostatic voltmeter can be used to measure the voltage above the surface due to the presence of the electrets bound charges. A front to back voltage of 600 volts is possible for Teflon about 2 mills thick If a Teflon electret is then exposed to polar molecules, the surface voltage will quickly disappear as the surface is "wet." During wetting, polar molecules will cluster around bound surface charges in such a way that the charges of the adsorbed molecules and surface molecules cancel. If the wet surface is then wiped clean with a soft lint free tissue, the voltage above the electret will reappear.

The phenomena just described can be used to monitor the removal or deposition of adsorbed polar molecules on a standard electret surface. Such removal monitoring can be used, for example, to evaluate the effectiveness of various cleaning technologies. The dipole moment of various molecules can also be measured since non polar molecules will tend not to adhere to an electret, whereas highly polar molecules will attach themselves tenaciously to an electret surface and will be difficult to remove. Another useful application involves monitoring the buildup of molecular contaminants. This is especially useful in space applications (RFP SDIO84-91-R-0005). As molecular contaminants, such as station keeping propellants, build up on sensitive components, the amount of molecular coverage can be monitored.

Finally, it should be noted that although polar molecule detection is believed to be due to the mechanisms above, I do not wish to be bound by this.

OBJECTS AND ADVANTAGES

Several objects and advantages of the present invention are:

(a) to provide a fast method of detecting adsorbed polar molecules;
(b) to provide an inexpensive table top apparatus for detecting polar molecules.

Still further objects and advantages will become apparent from a consideration of the ensuing description and drawings.

Figure 1:
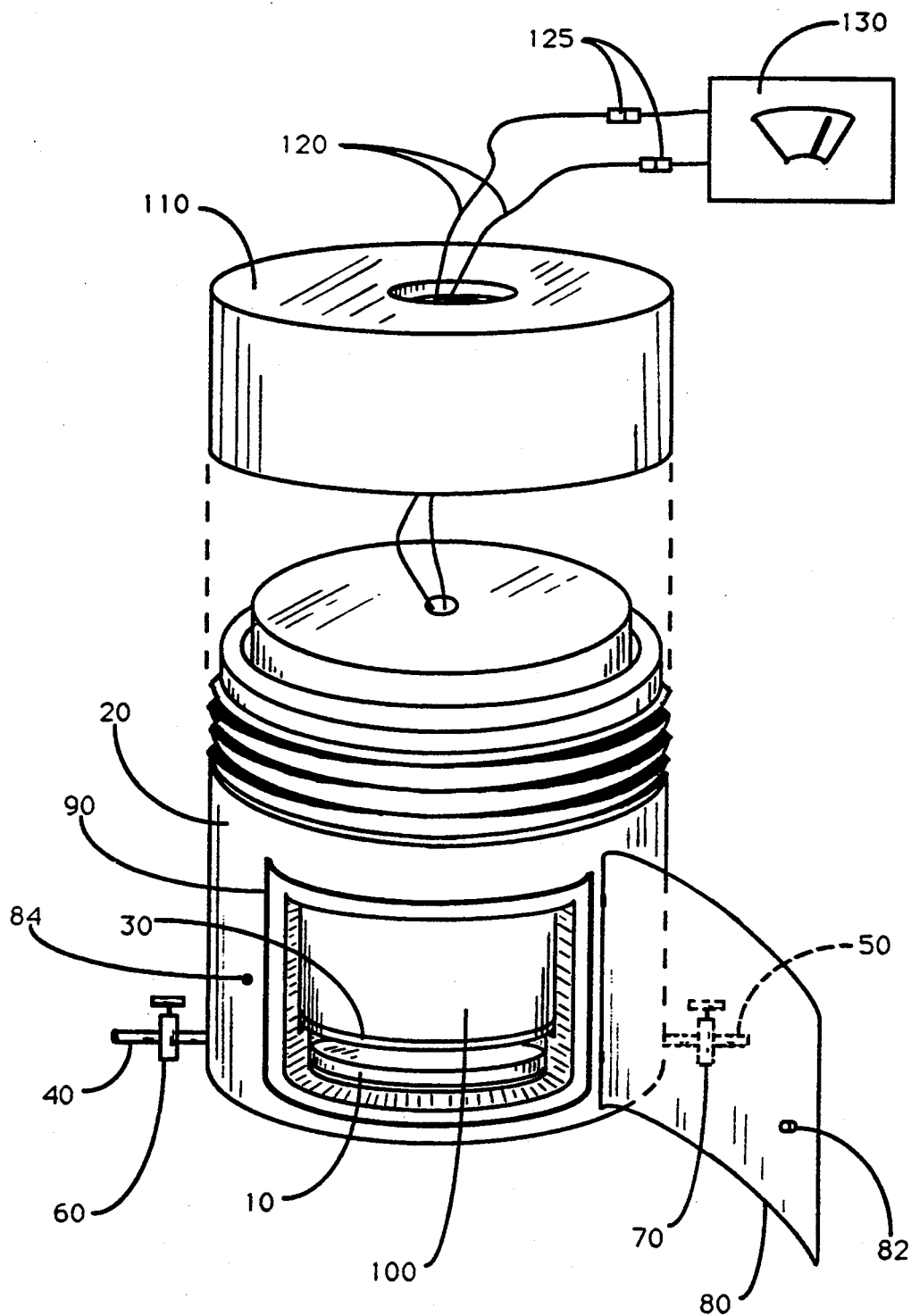
FIG. 1 shows an oblique view of the invention.
Figure 2:
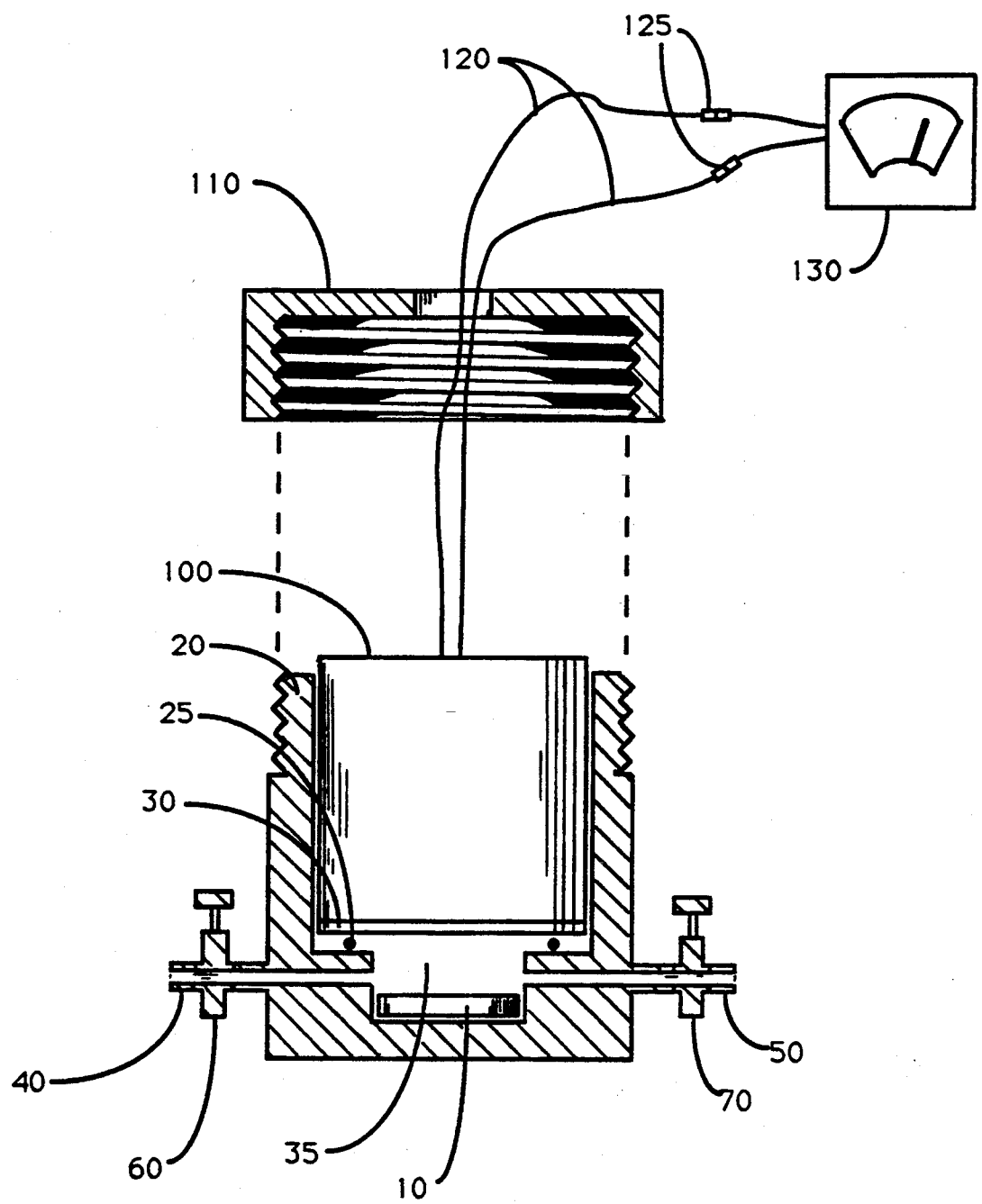
FIG. 2 shows a cross sectional side view of the invention.

REFERENCE NUMERALS IN DRAWING 10 substrate
20 holder
25 O-ring
30 window
35 chamber
40 inlet tube
50 outlet tube
60 inlet valve
70 outlet valve
80 door
82 screw
84 threaded hole
90 large O-ring
100 sensor head
110 cover
120 wires
125 electrical connectors
130 electrostatic voltmeter

DESCRIPTION—FIGS. 1 AND 2

The heart of the invention consists of a substrate 10 which is an electret, and is usually, but not necessarily, made of acrylic plastic or Teflon-brand PTFE (Teflon is a trademark of E. I. duPont de Nemours & Co., Wilmington, Del.) polymer. The substrate is prepared by placing it on a ground plate and heating it to a temperature of about 100° C. However, different polymers require different temperatures. While the polymer is being heated a strong electric fields of about 30,000 volts per cm is applied above the polymer. Again different polymers require different polarizing voltages. Finally the polymer is allowed to cool down to room temperature by removing the heat source while the electric field is still being applied. Once the polymer is restored to room temperature the electric field can be removed. Typically, polymer substrate 10 is disk shaped and may be anywhere from about 1 mil thick to about 1 cm thick, and has a diameter from about 1 cm to 15 cm. However, other dimensions and shapes for substrate 10 may be used.

Next, substrate 10 fits into a cavity at the bottom of a holder 20 which is preferably made of an insulating nonpolarizable material so that the front and back surfaces of substrate 10 will not be short circuited, thereby destroying the surface fields. An O-ring 25 sits upon a shoulder in the interior of holder 20, and a window 30 sits upon O-ring 25. Window 30 should be made of glass or some other, preferably inert, nonconducting material. A chamber 35 is thus formed, within which samples of gas, liquid, or particles, may enter through inlet tube 40. Samples may be removed through outlet tube 50 by a suction pump or by applying a positive gauge pressure to inlet tube 40. Chamber 35 may also be sealed off from the environment via an inlet valve 60 and an outlet valve 70. Substrate 10 can also be exposed to the environment by opening a door 80 which is sealed against the body of holder 20 by a large O-ring 90. Door 80 is secured in the closed position by a screw 82 which fits into threaded hole 84. Above window 30 lies a sensor head 100. The whole assembly is then held together by screwing on a cover 110. Cover 110 has a hole in it so that wires 120 from sensor head 100 can pass out of the apparatus to a pair of electrical connectors 125. Electrical connectors 125 allow wires of any convenient length to be connected to the apparatus so that signals transmitted along wires 120 can be sent to an electrostatic voltmeter 130 for display and possible recording. Electrostatic voltmeter 130 can be of the type having a moving needle display, or it can be a chart recorder. Electrostatic voltmeter 130 can also be a computer with analogue to digital conversion capability, a monitor for visual display of the data, and disk drives to record the data. This latter option is particularly attractive because it allows several detectors to be monitored simultaneously by multiplexing the incoming signals. Other types of electrostatic voltmeters 130 are possible as well.

OPERATION—FIGS 1 AND 2

Before commencing operation, it is first necessary to clean substrate 10. This is accomplished by removing substrate 10 from holder 20 and rubbing it with a clean dry cloth. The substrate is removed by disconnecting wires 120 at electrical connectors 125. Next, unscrew cover 110 and remove sensor head 100. The window 30, O-ring 25 and substrate 10 can now be removed. It is also a good practice to rub clean window 30, O-ring 25, and the bottom of holder 20, as well as substrate 10 when preparing to make measurements. The apparatus can now be used in two modes. In the first mode of operation substrate 10 is purposely contaminated with some chemical of interest to study the chemicals dipole moment or rate of removal by cleaning techniques. The contaminated substrate 10 is simply put back into the apparatus with inlet valve 60 closed, outlet valve 70 closed, and door 80 closed. When electrostatic voltmeter 130 is activated, sensor head 100 will relay a signal to electrostatic voltmeter 130 which can be read off its display device. The other mode of operation requires putting the clean substrate back into holder 20 with either inlet valve 60 and outlet valve 70 both open and door 80 closed, or door 80 open and the inlet valve 60 and outlet valve 70 closed. Electrostatic voltmeter 130 can now monitor the rate of deposition of contaminants on substrate 10 as a function of time. It has been determined experimentally that a quantity C, defined as the difference between the clean substrate voltage and the contaminated substrate voltage divided by the clean substrate voltage, is proportional to the amount of adsorbed material on the surface. The quantity C varies between 0 and 1. A zero value indicates no adsorption of molecules, whereas unity indicates complete saturation of the surface. The display on electrostatic voltmeter 130 can be designed to display C, a voltage relative to ground, or both. Other displays are also possible, including the percent area of coverage.

SUMMARY, RAMIFICATIONS, AND SCOPE

Accordingly, the reader will see that the device described in this invention provides a compact, fast, inexpensive method of detecting molecular contaminants and their buildup. Although the description above contains many specificities, these should not be considered as limiting the scope of the invention but as merely providing illustrations of some of the presently preferred embodiments of this invention.

For example, substrate 10 can have various sizes, shapes, and thicknesses. Furthermore, any number of different types of material can be used for substrate 10, not just Teflon or acrylic. Similarly, holder 20 can have a shape other than cylindrical so as to accommodate a different substrate shape. Other minor variations include a snap on cap instead of a screw on cover. It is even possible to leave of the cover in many applications. Also, door 80 can be omitted, or door 80 can be present and inlet tube 40, outlet tube 50, inlet valve 60, and outlet valve 70 can be omitted. Door 80 can also have another type of fastening mechanism instead of screw 82 and threaded hole 84. In cases where it is only necessary to contaminate the electret substrate 10 and then measure the field change, such as in dipole moment measurements, door 80, inlet tube 40, inlet valve 60, outlet tube 50, and outlet valve 70 can all be omitted. Finally, electrostatic voltmeter 130 can be replaced by a chart recorder, computer, or another recording and display device.

Thus the scope of the invention should be determined by the appended claims and their legal equivalents, rather than by the examples given.

I claim:
1. A device for detecting molecules consisting of:
   a) an electric field producing electret substrate upon which molecules can be collected;
   b) holder within which said substrate is placed;
   c) a sensor head which fits within said holder, whereby the electric field above said substrate is measured; and
   d) an electrostatic voltmeter electrically connected to said sensor head, whereby the electric field measurements above said substrate is made including means indicating the percent area of coverage of the substrate by the molecules being detected.

* * * * *